(12) United States Patent
Kuebel

(10) Patent No.: US 8,196,448 B2
(45) Date of Patent: Jun. 12, 2012

(54) HYDROGEN SENSOR ASSEMBLY

(75) Inventor: Christoph Kuebel, Wiesbaden (DE)

(73) Assignee: GM Global Technology Operations LLC, Detroit, MI (US)

( * ) Notice: Subject to any disclaimer, the term of this patent is extended or adjusted under 35 U.S.C. 154(b) by 255 days.

(21) Appl. No.: 12/690,618

(22) Filed: Jan. 20, 2010

(65) Prior Publication Data

US 2011/0174052 A1    Jul. 21, 2011

(51) Int. Cl.
  *G01N 7/00* (2006.01)
  *G01N 27/00* (2006.01)
(52) U.S. Cl. .................. 73/23.31; 73/31.05; 422/98
(58) Field of Classification Search ............ 422/94, 422/98, 68.1; 73/23.31, 31.01, 31.02, 31.03, 73/31.05, 31.07
See application file for complete search history.

(56) References Cited

U.S. PATENT DOCUMENTS

| | | | |
|---|---|---|---|
| 4,745,796 A * | 5/1988 | Abdelrahman et al. ..... | 73/31.07 |
| 5,979,219 A * | 11/1999 | Sellmer-Wilsberg et al. ............... | 73/19.12 |
| 6,647,783 B2 * | 11/2003 | Wewers et al. ................. | 73/431 |
| 7,269,993 B2 * | 9/2007 | Oishi et al. .................... | 73/23.31 |
| 2008/0175759 A1 * | 7/2008 | Oishi et al. ....................... | 422/98 |
| 2009/0061261 A1 * | 3/2009 | Hatta et al. ....................... | 429/12 |
| 2010/0077828 A1 * | 4/2010 | Herz et al. ..................... | 73/1.03 |
| 2011/0226039 A1 * | 9/2011 | Roland et al. ................ | 73/23.31 |

FOREIGN PATENT DOCUMENTS

| | | |
|---|---|---|
| CA | 2618786 A1 | 2/2007 |
| DE | 19503802 C1 | 3/1996 |
| DE | 102004011731 A1 | 9/2004 |
| DE | 112005000251 T5 | 3/2007 |
| EP | 0124818 B1 | 1/1990 |

* cited by examiner

*Primary Examiner* — Lisa Caputo
*Assistant Examiner* — Punam Roy
(74) *Attorney, Agent, or Firm* — Fraser Clemens Martin & Miller LLC; J. Douglas Miller

(57) ABSTRACT

A hydrogen sensor assembly is disclosed. The hydrogen sensor assembly includes a sensing element within a sensor housing. The sensor housing includes an opening to facilitate a fluid communication between the sensing element and an exhaust stream of a fuel cell. A substantially water-vapor-impermeable membrane is disposed within the opening between the sensing element and the exhaust stream to militate against water vapor from the exhaust stream entering the sensor housing. The sensor housing may include a second opening to facilitate a fluid communication between the sensing element and an external environment to evacuate water vapor generated by the sensing element.

16 Claims, 1 Drawing Sheet

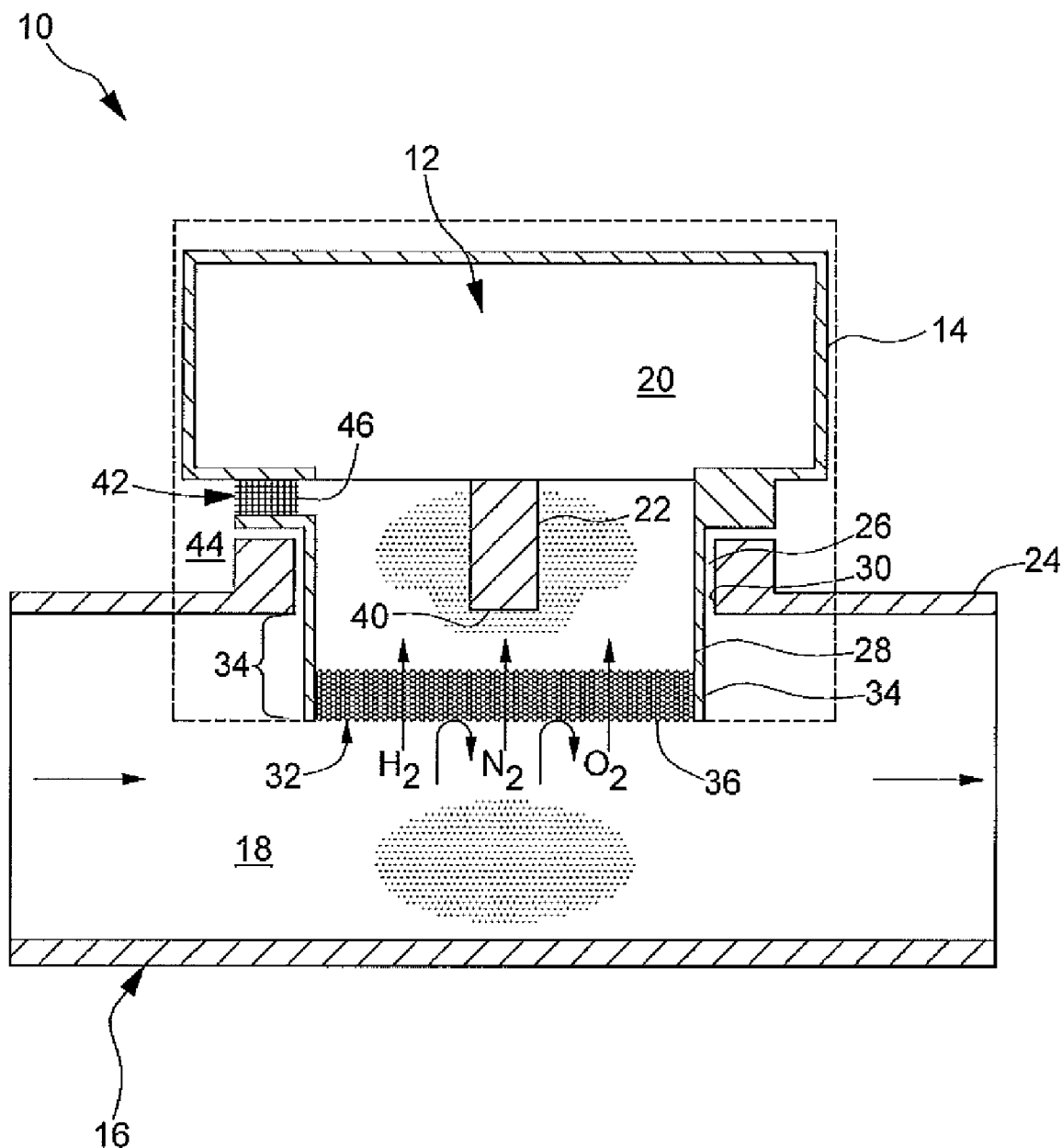

HYDROGEN SENSOR ASSEMBLY

FIELD OF THE INVENTION

The invention relates to fuel cell systems. More particularly, the invention relates to a hydrogen sensor assembly for measuring a concentration of hydrogen in a fuel cell exhaust stream.

BACKGROUND OF THE INVENTION

Electrochemical fuel cells are generally known in the art and convert fuel and an oxidant to electricity. One such fuel cell is a solid polymer electrochemical cell and includes a plurality of membrane electrode assemblies (MEA), each of which includes an ion exchange membrane or other electrolyte disposed between an anode and cathode. The MEA may include a catalyst or other catalytic material at each interface between the ion exchange membrane and the anode to induce a desired electrochemical reaction. The electrodes are electrically coupled to provide a circuit for conducting electrons between the anodes and the cathodes through an external circuit.

In a hydrogen powered fuel cell, hydrogen and air are supplied to electrodes on either side of the ion exchange membrane. Hydrogen is typically supplied to the anode where the catalyst promotes a separation into protons and electrons that are conducted through the external circuit. On the opposing side of the membrane, air is provided to the cathode where oxygen in the air reacts with the protons passing through the ion exchange membrane to produce byproduct water.

The hydrogen fuel fluid stream supplied to a fuel cell anode may be, for example, substantially pure hydrogen, or a dilute hydrogen stream such as a reformate stream. Further, the anode exhaust stream containing unreacted hydrogen, or a portion thereof, may be recirculated back to the fuel cell, depending upon a measured concentration of unreacted hydrogen contained in the exhaust stream. It is known to provide hydrogen sensors operably associated with a fuel cell exhaust stream for measuring a concentration of hydrogen in the exhaust stream. Further, the concentration of hydrogen within the exhaust stream may be used as an indicator of the fuel cell performance and operating efficiency. For example, if there is an excessive amount of hydrogen in the fuel stream exhausted from the fuel cell, it may indicate poor operating efficiency.

However, fuel cell exhaust gasses consist of nitrogen, trace hydrogen and water vapor at a temperature of approximately 70° C. (158° F.) with nearly 100% relative humidity. This high absolute humidity generates condensate inside the hydrogen sensor, which may result in temporary or permanent incorrect hydrogen concentration readings. Additionally, chemical hydrogen sensors, such as those used in current fuel cell vehicles, generate water vapor by themselves due to a reaction of free hydrogen with oxygen on the surface of the sensor while detecting the hydrogen concentration.

Available hydrogen concentration sensors are designed for ambient application and usage in low humidity environments. It is known that use of available sensors in high humidity environments where condensation may occur adversely impacts the lifetime and reliability of the sensor. The combination of high temperature and high humidity within the sensor assembly may lead to corrosion or degradation of the sensor or components and wiring thereof, requiring premature and costly replacement of the sensor. Moreover, it has been determined that condensed water inside the hydrogen sensor is a primary reason for diminished reliability and durability of the sensor.

Use of available hydrogen concentration sensors for fuel cell exhaust gas applications does not meet automotive requirements for durability, reliability and cost. Presently, a primary method of addressing the drawbacks of current sensor technology is to make frequent prophylactic exchanges or replacements of the hydrogen sensor after a relatively limited number of operational hours, which is a cost intensive measure. The high frequency of the sensor exchange rate impacts a vehicle's reliability, removes it from service frequently for sensor replacement, and increases the servicing or lifetime costs of the vehicle.

There is a continuing need for a cost effective, long lifetime hydrogen concentrations sensor assembly that militates against water vapor condensation inside the sensor housing.

SUMMARY OF THE INVENTION

Concordant and consistent with the present invention, a hydrogen sensor assembly that militates against water vapor condensation inside a hydrogen sensor to thereby minimize degradation of the hydrogen sensor and maximize the reliability thereof has surprisingly been discovered.

In one embodiment, a hydrogen sensor assembly includes a sensing element within a sensor housing, the sensor housing including an opening to facilitate a fluid communication between the sensing element and an exhaust stream of a fuel cell, a substantially water-vapor-impermeable membrane disposed within the opening between the sensing element and the exhaust stream to militate against water vapor from the exhaust stream entering the sensor housing.

In another embodiment, the sensor housing includes a second opening to facilitate a fluid communication between the sensing element and an external environment to remove water vapor generated by the sensing element. A second, water-vapor-permeable membrane may be disposed within the second opening to prevent contaminants from entering the sensor housing and to facilitate evacuation of water vapor from within the sensor housing.

BRIEF DESCRIPTION OF THE DRAWINGS

The above, as well as other advantages of the present invention, will become readily apparent to those skilled in the art from the following detailed description of the preferred embodiment when considered in the light of the accompanying drawing, which is a schematic cross-sectional elevational view of a hydrogen sensor assembly according to an embodiment of the present invention.

DETAILED DESCRIPTION OF EXEMPLARY EMBODIMENTS OF THE INVENTION

The following detailed description and appended drawings describe and illustrate various embodiments of the invention. The description and drawings serve to enable one skilled in the art to make and use the invention, and are not intended to limit the scope of the invention in any manner.

A sensor assembly 10 is shown in the drawing. The sensor assembly 10 includes a hydrogen sensor 12 in a sensor housing 14. The sensor housing is located adjacent an exhaust gas plenum 16 and in fluid communication therewith. An exhaust gas stream 18 flows through the exhaust gas plenum 16, and includes trace levels of free hydrogen ($H_2$) and free oxygen ($O_2$), nitrogen ($N_2$), water vapor, and various contaminants.

As noted previously, the exhaust gas stream 18 within the exhaust gas plenum 16 flows at a temperature of approximately 70° C. (158° F.) with nearly 100% relative humidity. As a result, a very small temperature drop within the plenum 16 or within the sensor housing 14 will result in condensation of water.

Within the housing 14 of the hydrogen sensor 12, various electronics 20 are packaged, depending upon the type of the sensor being used. The electronics 20 are electrically coupled to a sensing element 22. It is understood that the sensing element 22 may be any type of sensing element. However, for purposes of illustration, the sensing element 22 is a hydrogen sensor. Conventionally, fuel cells for motor vehicle applications utilize a chemical-type sensing element 22 that relies on a reaction between free oxygen and free hydrogen to detect hydrogen concentrations. However, the sensing element 22 may be a non-porous metal oxide type, a metal-oxide semiconductor type, or other sensing element known in the art. It is further understood that the electronics 20 are adapted to convert a signal received from the sensing element 22 into data representing a hydrogen concentration level.

The exhaust gas plenum 16 includes an exterior wall 24 with an opening 26 defined therethrough. The opening 26 is sized to mate with an exterior portion 28 of the sensor housing 14. A seal (not shown) may be disposed between the exterior portion 28 of the sensor housing 14 and a surface 30 defining the opening 26 to ensure a fluid-tight engagement between the sensor housing 14 and the exterior wall 24 of the exhaust gas plenum 16, to thereby militate against any portion of the exhaust gas stream 18 from escaping through the opening 26. When the sensor housing 14 is inserted into the opening 26 in the exhaust gas plenum 16, an appropriately sized opening 32 in the inserted portion 34 of the sensor housing 14 facilitates placing the sensing element 22 in fluid communication with the exhaust gas stream 18.

Known types of sensing elements 22 are not compatible with high humidity environments, and have limited lifetimes when exposed to high water vapor concentrations. Therefore, a substantially water-vapor impermeable membrane 36, such as polytetrafluoroethylene (PTFE) or other suitable membrane known in the art, is disposed in the opening 32 in the sensor housing 14. The substantially water-vapor impermeable membrane 36 is interposed between the exhaust gas stream 18 and the sensing element 22 to minimize the exposure of the sensing element 22 to water vapor within the exhaust gases 18. It is understood that the membrane 36 is substantially impermeable to water vapor, but is not substantially impermeable to other constituent component parts of the exhaust gas stream 18, such as hydrogen, oxygen, nitrogen, and the like. The sensing element 22 is therefore sufficiently exposed to the exhaust gas stream 18, and is capable of accurately measuring hydrogen concentrations within the exhaust gas stream 18 without any deleterious effects on the sensing element 22 due to water exposure including incorrect hydrogen concentration readings, corrosion, degradation of the sensor, or freezing of the sensor during periods of non-operation of the fuel cell.

In operation of the hydrogen sensor 12, the sensing element 22 measures a hydrogen concentration by detecting oxidation of free hydrogen, or by otherwise reacting hydrogen on the surface 40 of the sensing element 22. The oxidation reaction of hydrogen produces water vapor within the hydrogen sensor housing 14 that is prevented from crossing the substantially water-vapor-impermeable membrane 36. To facilitate evacuation of the water vapor produced within the sensor housing 14, the hydrogen sensor 12 includes a second opening 42 in the sensor housing 14 that facilitates placing the sensing element 22 in fluid communication with an external environment 44. Favorable results have been found when the second opening 42 exposes the sensing element 22 to the ambient environment. To prevent contamination inside the hydrogen sensor 12, a substantially water-vapor-permeable membrane 46 of a type known in the art may be disposed within the second opening 42 to allow evacuation of water vapor formed within the hydrogen sensor 12 due to oxidation of the free hydrogen from the exhaust gas stream 18. The substantially water-vapor-permeable membrane 46 may be chosen to facilitate evacuation of the water vapor formed within the hydrogen sensor 12 due to a pressure gradient between the exhaust gas stream 18 and the external environment 44, or due to a humidity gradient between within the hydrogen sensor housing 14 and the external environment 44. The second opening 42 minimizes the exposure of the sensing element 22 to water vapor, thereby increasing the reliability, durability and longevity of the hydrogen sensor 12. Frequent prophylactic replacement of the hydrogen sensor may therefore be eliminated.

From the foregoing description, one ordinarily skilled in the art can easily ascertain the essential characteristics of this invention and, without departing from the spirit and scope thereof, make various changes and modifications to the invention to adapt it to various usages and conditions.

What is claimed is:

1. A hydrogen sensor assembly, comprising:
   a sensing element disposed within a sensor housing, the sensor housing including
     a first opening to facilitate a fluid communication between the sensing element and a fluid stream, and
     a second opening to facilitate a fluid communication between the sensing element and an external environment;
   a substantially water-vapor-impermeable membrane disposed within the first opening between the sensing element and the fluid stream to militate against water vapor from the fluid stream entering the sensor housing; and
   a substantially water-vapor-permeable membrane disposed within the second opening to militate against contaminants from the external environment entering the sensor housing.

2. The hydrogen sensor assembly of claim 1, wherein the substantially water-vapor-impermeable membrane is a polytetrafluoroethylene membrane.

3. The hydrogen sensor assembly of claim 2, wherein the fluid stream is a fuel cell exhaust stream.

4. The hydrogen sensor assembly of claim 1, wherein the substantially water-vapor-impermeable membrane is permeable by hydrogen, nitrogen and oxygen.

5. The hydrogen sensor assembly of claim 1, wherein the sensor housing is received in an aperture of a fuel cell exhaust plenum.

6. The hydrogen sensor assembly of claim 1, wherein the external environment is the ambient environment.

7. The hydrogen sensor assembly of claim 6, wherein the substantially water-vapor-permeable membrane facilitates evacuation of water vapor from within the sensor housing by one of a pressure gradient and a humidity gradient.

8. A hydrogen sensor assembly, comprising:
   a sensing element disposed within a sensor housing, the sensor housing including a first opening to facilitate a fluid communication between the sensing element and a fluid stream;

a substantially water-vapor-impermeable membrane disposed within the first opening between the sensing element and the fluid stream to militate against water vapor from the fluid stream entering the sensor housing;

a second opening in the sensor housing to facilitate a fluid communication between the sensing element and an external environment; and a substantially water-vapor-permeable membrane disposed within the second opening to militate against contaminants from the external environment entering the sensor housing.

9. The fuel cell system of claim 8, wherein the substantially water-vapor-impermeable membrane is a polytetrafluoroethylene membrane.

10. The hydrogen sensor assembly of claim 8, wherein the substantially water-vapor-impermeable membrane is permeable by hydrogen, nitrogen and oxygen.

11. The hydrogen sensor assembly of claim 10, wherein the sensor housing is received in an aperture of a fuel cell exhaust plenum.

12. The fuel cell system of claim 11, wherein the substantially water-vapor-permeable membrane facilitates evacuation of water vapor from within the sensor housing by one of a pressure gradient and a humidity gradient.

13. A hydrogen sensor assembly, comprising:

a sensor housing having first and second apertures therein;

a sensing element disposed in the sensor housing in fluid communication with a fluid stream through the first aperture, and in fluid communication with the environment through the second aperture;

a substantially water-vapor-impermeable membrane disposed within the first aperture to militate against permeation of water vapor therethrough; and a substantially water-vapor-permeable membrane disposed within the second aperture to facilitate permeation of water vapor to the environment.

14. The hydrogen sensor assembly of claim 13, wherein the substantially water-vapor-impermeable membrane is permeable by hydrogen, nitrogen and oxygen.

15. The fuel cell system of claim 14, wherein the substantially water-vapor-impermeable membrane is a polytetrafluoroethylene membrane.

16. The hydrogen sensor assembly of claim 15, wherein the substantially water-vapor-permeable membrane facilitates evacuation of water vapor from within the sensor housing by one of a pressure gradient and a humidity gradient.

* * * * *